United States Patent
Oren (10) Patent No.: US 9,255,165 B2
(45) Date of Patent: Feb. 9, 2016

(54) POLY (PENTABROMOBENZYL ACRYLATE) AND ITS PROPERTIES

(71) Applicant: BROMINE COMPOUNDS LTD., Be'er-Sheva (IL)

(72) Inventor: Jacob Oren, Nesher (IL)

(73) Assignee: BROMINE COMPOUNDS LTD., Be'er-Sheva (IL)

( * ) Notice: Subject to any disclaimer, the term of this patent is extended or adjusted under 35 U.S.C. 154(b) by 0 days.

(21) Appl. No.: 14/637,016

(22) Filed: Mar. 3, 2015

(65) Prior Publication Data

US 2015/0191559 A1    Jul. 9, 2015

Related U.S. Application Data (62) Division of application No. 14/110,943, filed as application No. PCT/IL2012/000154 on Apr. 5, 2012, now Pat. No. 9,018,324.

(60) Provisional application No. 61/475,234, filed on Apr. 14, 2011.

(51) Int. Cl.
| | |
|---|---|
| C08F 22/10 | (2006.01) |
| C08F 120/22 | (2006.01) |
| C07C 67/14 | (2006.01) |
| C08F 220/22 | (2006.01) |
| C08F 220/68 | (2006.01) |

(52) U.S. Cl.
CPC ............... C08F 22/10 (2013.01); C07C 67/14 (2013.01); C08F 120/22 (2013.01); C08F 220/22 (2013.01); C08F 220/68 (2013.01)

(58) Field of Classification Search
CPC ...... C08F 22/10; C08F 120/22; C08F 220/22; C08F 220/68; C07C 67/14
USPC .......................... 526/89, 292.5, 319; 560/221
See application file for complete search history.

(56) References Cited

U.S. PATENT DOCUMENTS

| | | | |
|---|---|---|---|
| 4,059,618 A | | 11/1977 | Blumenfeld et al. |
| 4,128,709 A | * | 12/1978 | Vollkommer ........... C08F 20/22 260/DIG. 24 |
| 4,996,276 A | | 2/1991 | Fishler et al. |
| 6,028,156 A | * | 2/2000 | Peled .................... C08F 120/06 526/208 |
| 7,601,774 B2 | | 10/2009 | Kornberg et al. |
| 2005/0124829 A1 | | 6/2005 | Beruben |

FOREIGN PATENT DOCUMENTS

| | | |
|---|---|---|
| CN | 1646471 | 7/2005 |
| DE | 25 27 802 | 12/1976 |

OTHER PUBLICATIONS

International Search Report for PCT/IL2012/000154 mailed Aug. 10, 2012.
Written Opinion of the International Searching Authority in PCT/IL2012/000154 mailed Aug. 10, 2012.
Chinese Office Action issued in Application No. 201280028767.4 dated Feb. 2, 2014 (partial translation).
Prior Art Product FR-1025, http://icl-ip.com/products/fr-1025/, ICL Industrial Products (Bromine Compounds, Ltd.) Poly(pentabromobenzyl acrylate) known as FR-1025 is produced by means of bulk polymerization in a twin-screw extruder and has molecular weight higher than 400,000 (e.g., 600,000) and high polydispersity index, above 20, determined by high temperature gel permeation chromatography method reported in the patent application. (available before Jan. 1, 2010).
Shuying Ren, "Study on poly (pentabromobenzyl acrylate)," Plastic Additives, Dec. 1998, pp. 7-10, No. 6.

* cited by examiner

*Primary Examiner* — Michael M Bernshteyn
(74) *Attorney, Agent, or Firm* — Nixon & Vanderhye P.C.

(57) ABSTRACT

Poly (pentabromobenzyl acrylate) having a weight average molecular weight (Mw) in the range from 200,000 to 600,000 and a polydispersity index less than 15 based on high temperature gel permeation chromatography.

3 Claims, 2 Drawing Sheets

POLY (PENTABROMOBENZYL ACRYLATE) AND ITS PROPERTIES

This application is a divisional of Ser. No. 14/110,943, filed Oct. 10, 2013, now U.S. Pat. No. 9,018,324, which is the U.S. national phase of International Application No. PCT/IL2012/000154, filed Apr. 5, 2012 which designated the U.S. and claims priority to U.S. Provisional Application No. 61/475,234, filed Apr. 14, 2011, the entire contents of each of which are hereby incorporated by reference.

Pentabromobenzyl acrylate is a monomer useful for the production of poly (pentabromobenzyl acrylate), a polymer which is used as a flame retardant agent in flammable materials. The monomer and the polymer, abbreviated herein PBBMA and PBBPA, respectively, are represented by the following formulas:

In its most general form, the route of synthesis of pentabromobenzyl acrylate is based on the reaction between pentabromobenzyl halide (i.e., chloride or bromide) with a salt of acrylic acid, e.g., sodium acrylate.

The preparation of pentabromobenzyl acrylate is disclosed in U.S. Pat. No. 4,059,618, where acrylic acid is transformed to its sodium salt in a polar organic solvent, such as ethylene glycol monomethyl ether, followed by the addition of pentabromobenzyl chloride. The reaction is accomplished in the presence of a polymerization inhibitor.

In U.S. Pat. No. 4,128,709 a similar procedure is described, followed by the radical polymerization of the resultant monomer in methyl glycol to give poly(pentabromobenzyl acrylate).

In U.S. Pat. No. 6,028,156 a preparative procedure for making pentabromobenzyl acrylate is disclosed, employing methyl ethyl ketone as the solvent. Having formed a slurry of sodium acrylate in methyl ethyl ketone, pentabromobenzyl halide is added, to give PBBMA. U.S. Pat. No. 6,028,156 further describes a reaction between pentabromobenzyl bromide and sodium acrylate in chlorobenzene/water system in the presence of a phase transfer catalyst. More specifically, Example 5 of U.S. Pat. No. 6,028,156 illustrates the one-pot synthesis of pentabromobenzyl acrylate, starting from pentabromotoluene, which is brominated in chlorobenzene to give pentabromobenzyl bromide (sometimes abbreviated herein PBBBr), which in turn reacts with sodium acrylate formed in situ through the gradual addition of acrylic acid into the reaction vessel, to which an aqueous solution of a base and phase transfer catalyst had been charged. Having completed the gradual addition of the acrylic acid, the reaction mixture is heated and maintained under heating for a few hours, during which period of time the reaction proceeds and reaches completion.

Having investigated the progress of the reaction between pentabromobenzyl bromide and sodium acrylate carried out in a two phase system consisting of chlorobenzene and water, in the presence of a phase transfer catalyst, it has been observed that the conversion of the PBBBr starting material under the conditions when sodium acrylate is being generated in situ, followed by a heating stage until the reaction is completed, proceeds rapidly at the beginning of the heating stage, but later on slows down. For example, although a conversion of about 90-95% can be achieved within the first hour of the heating stage, still, a few more hours are required to complete the reaction, in order to arrive at an acceptable conversion of PBBBr (~99.5% conversion).

It has been now found that it is possible to shorten significantly the duration of the reaction through the separation of the reaction mixture into organic and aqueous phases towards the end of the reaction, for example, when the conversion of PBBBr achieved is less than 95%, say, between 80 and 95%, and the removal of the aqueous phase. The organic phase is collected and then combined with a salt of acrylic acid in an aqueous form, followed by heating, whereby the reaction rapidly reaches completion. It is believed that towards the end of the reaction, an appreciable accumulation of the sodium bromide by-product which takes place in the aqueous phase interferes with the progress of the reaction and prevents the reaction from reaching completion at an acceptable rate. The removal of the sodium bromide-containing aqueous phase, which is formed during the conversion of the first 80-95% of the PBBBr starting material, and the combination of the organic phase (which contains the product and about 5-20% of unreacted PBBBr starting material) with fresh aqueous sodium acrylate, followed by a short period of heating, rapidly brings the reaction to completion.

It has also been found that it is possible to prepare in advance a suitable aqueous solution of a salt of acrylic acid, e.g., a solution of sodium acrylate with an adequate composition, which retains its stability under storage over time and can be used in the reaction in place of an in situ generated sodium acrylate. Thus, sodium acrylate can be supplied to the reaction in the form of an aqueous solution, by means of separately charging two or more portions of said solution into the reaction vessel, thereby dividing the process into two (or more) stages, wherein each stage consists of combining pentahalobenzyl halide with a suitable amount of an aqueous solution of sodium acrylate, in a medium consisting of a water immiscible organic solvent, water and a phase transfer catalyst, maintaining the reaction mixture under heating, separating the reaction mixture into organic and aqueous phases, removing the aqueous phase, and transferring the organic phase containing unreacted pentahalobenzyl halide to the next stage, where it contacts with a fresh aqueous solution of sodium acrylate.

The present invention is therefore directed to a process comprising reacting pentahalobenzyl halide with a salt of acrylic acid in water-immiscible solvent, wherein said salt is in aqueous form and the reaction is carried out in the presence of a phase transfer catalyst, separating the reaction mixture into organic and aqueous phases prior to the completion of the reaction, removing the aqueous phase and collecting the organic phase which contains unreacted pentahalobenzyl halide, and allowing the reaction to reach completion through one or more successive reaction stages, wherein each of said one or more successive reaction stages comprises combining an organic phase separated from a previous reaction stage with an aqueous solution comprising a salt of acrylic acid, and recovering the pentahalobenzyl acrylate product.

The process of the invention preferably comprises:

providing an aqueous solution of an alkali salt of acrylic acid;

charging a reaction vessel with a water immiscible organic solvent, pentahalobenzyl halide (e.g., pentabromobenzyl bromide), a phase transfer catalyst and a first amount of said aqueous alkali acrylate salt, to form a first reaction mixture;

gradually heating said first reaction mixture and maintaining same under heating for a first period time;

separating said first reaction mixture into a first organic phase and a first aqueous phase; collecting said first organic phase;

combining said first organic phase with a second amount of aqueous alkali acrylate salt, to form a second reaction mixture; and maintaining said second reaction mixture under heating for a second period of time, and optionally isolating the pentahalobenzyl acrylate product (e.g., pentabromobenzyl acrylate).

The preferred reactants involved in the process of the invention (an aqueous solution of sodium acrylate and pentahalobenzyl halide), the reagents used (a water-immiscible solvent and a phase transfer catalyst), and the conditions employed in the process are now described in more detail, with reference to the following reaction scheme, which illustrates a preferred embodiment of the invention, consisting of the preparation in advance of sodium acrylate in an aqueous form, followed by the reaction of pentabromobenzyl bromide with said sodium acrylate, to give pentabromobenzyl acrylate, as shown by Scheme 1:

Sodium acrylate is used in an aqueous form. To this end, an aqueous sodium acrylate solution (herein sometimes abbreviated NaA) is preferably prepared in a separate reaction vessel, by the controlled addition of a concentrated aqueous sodium hydroxide solution (e.g., 48% NaOH solution) to an aqueous solution of acrylic acid at 10-50° C. The concentration of the acrylic acid solution is between 25 and 40%. The reaction is a titration of an acid with a base, and can be reliably monitored under pH control. The addition of the base is suitably adjusted such that a nearly neutral solution of sodium acrylate is obtained, with a pH of approximately 6 to 7, indicating that the molar ratio between the sodium acrylate and the acrylic acid in the solution is from 94:6 to 99:1, preferably from 97:3 to 98:2. A solution which contains about 35±2% w/w NaA and about 0.7±0.1% w/w acrylic acid, having a pH around 6.3, has been found especially useful in the process of the invention, providing the optimal consumption of NaA to the production of PBBMA. The NaA solution can be held at room temperature (at <30° C. and protected from light to prevent polymerization) for at least a few days before use in the process of the invention.

The pentahalobenzyl halide reactant used in the second chemical reaction depicted in Scheme 1 above is preferably pentabromobenzyl bromide, which can be prepared by methods known in the art (e.g., U.S. Pat. No. 6,028,156 and U.S. Pat. No. 7,601,774), according to the route of synthesis involving the aromatic bromination of toluene, for example in halogenated solvent(s), using elemental bromine, in the presence of a Lewis acid catalyst, e.g. AlCl₃, to form pentabromotoluene (abbreviated herein 5-BT), which is then brominated at the benzylic carbon using elemental bromine, as illustrated by the following scheme (see U.S. Pat. No. 7,601,774):

The radical bromination reaction of pentabromotoluene is carried out in the presence of a suitable catalyst, such as 2,2-azodi-isobutyronitrile (AIBN), as illustrated in Example 5 of U.S. Pat. No. 6,028,156. However, it has now been found that dibenzoyl peroxide (DBP) can be used instead of AIBN as a catalyst in the bromination reaction of pentabromotoluene to give high purity pentabromobenzyl bromide (e.g., of not less than 99.3%, as indicated by HPLC analysis).

Accordingly, in a preferred embodiment, the pentabromobenzyl bromide used in the preparation of pentabromobenzyl acrylate according to the process of the invention is obtained by the radical bromination of pentabromotoluene in halogenated solvent, e.g., halogenated aromatic solvent such as chlorobenzene, in the presence of dibenzoyl peroxide.

In order to carry out the radical bromination of pentabromotoluene, a reaction vessel is charged with organic solvent, pentabromotoluene, water, elemental bromine and the catalyst dibenzoyl peroxide. The weight ratios between the preferred organic solvent (chlorobenzene), the pentabromotoluene starting material and the water are preferably about 1:1:1. Elemental bromine is used in a molar excess relative to the pentabromotoluene starting material, e.g., an excess of 15-25 mole %. The catalyst loading is preferably between 0.5 and 2% w/w, preferably between 0.8 and 1.6% w/w, relative to the amount of pentabromotoluene, and is more preferably around 1% w/w. Having introduced the reactants and reagents into the reaction vessel, the reaction mixture is heated to about 80-90° C., and kept at this temperature range for about 3-5 hours. The progress of the reaction can be monitored through GC analysis. The reaction mixture is cooled to about 50° C., and excess bromine is neutralized by the addition of a reducing agent, such as sodium bisulfate, which is conveniently employed in the form of an aqueous solution. The reaction mixture is then further cooled to about room temperature, following which the aqueous phase is removed from the reaction mixture and an aqueous alkaline solution (e.g., sodium carbonate) is added to the slurry to neutralize the acidity (HBr is a by-product of the reaction). The solid product can be isolated from the liquid phase by conventional methods, such as filtration, followed by washing and drying. The pure pentabromobenzyl bromide thus obtained can be used as the raw material in the synthesis of pentabromobenzyl acrylate.

Water immiscible organic solvents which can be employed in the reaction between the pentahalobenzyl halide and the aqueous sodium acrylate include aromatic solvents, especially halogenated aromatic solvents, e.g., halogenated derivatives of benzene and toluene. Chlorobenzene (abbreviated CB in Scheme 1 shown above) is particularly preferred, due to the fact that it can be used in each of the synthetic steps involved in the sequential reaction, starting from pentabromotoluene and arriving at poly(pentabromobenzyl acrylate). Thus, not only the radical bromination reaction of pentabromotoluene to form pentabromobenzyl bromide, as shown in Scheme 2, and the transformation of the latter to pentabromobenzyl acrylate, as shown in Scheme 1, can be accomplished in chlorobenzene, but, unexpectedly, also the polymerization of pentabromobenzyl acrylate to produce the active flame retardant agent poly(pentabromobenzyl acrylate). This offers the advantage of running the sequential reaction from the beginning to the end using the same organic solvent, as discussed in more detail below.

The preferred phase transfer catalyst employed in the process of the invention, namely, in the second reaction according to Scheme 1, can be selected from the group consisting of tetraalkyl ammonium halides. Tetrabutylammonium bromide (TBAB) is preferably used, in the form of an aqueous solution, for example, at a concentration of 50% (w/w) (available commercially).

The second reaction according to Scheme 1 above is carried out by adding the water-immiscible organic solvent (e.g., chlorobenzene), the phase transfer catalyst (e.g., an aqueous solution of tetrabutylammonium bromide), the pentahalobenzyl halide starting material (e.g., pentabromobenzyl bromide) and a first amount of an aqueous solution of sodium acrylate into a stirred reactor at room temperature (20-30° C.), to form a first reaction mixture. The weight ratios between the organic solvent chlorobenzene and the pentabromobenzyl bromide is from 2:1 to 1:2, preferably between 0.9:1 and 1:0.9. The phase transfer catalyst is applied in an amount of 0.5 to 1.5% by weight to PBBBr. The first amount of the sodium acrylate solution is suitably adjusted such that the sodium acrylate is present in the first reaction mixture in molar deficiency relative to the pentabromobenzyl bromide, e.g., between 75 and 95% (molar %) based on pentabromobenzyl bromide. The initial pH of the first reaction mixture is around 6.5.

The first reaction mixture is then gradually heated to a temperature in the range from 92 to 98° C., preferably 94-95° C., over a period of not less than 60 minutes. The conversion of PBBBr achieved during this period of gradual heating is generally around 65-70%. The first reaction mixture is then kept under heating at said temperature range of about 94-95° C. for period of time (referred to herein as the first heating period and designated $t_1$), sufficient for achieving an essentially complete conversion of the sodium acrylate and correspondingly, a conversion of pentabromobenzyl bromide of about 75 and 95%, as may be determined by periodically sampling the reaction mixture and subjecting the samples to the HPLC analysis. By "an essentially complete conversion of the sodium acrylate" is meant that following the first heating period, the amount of the acrylate present in the aqueous phase is preferably less than 2%, based on the total weight of the aqueous NaA used. Preferably, the duration of the first heating period is less than 90 minutes, e.g., between 30 minutes and 90 minutes, and even less, namely, around 60-70 minutes.

Upon completing the first heating stage, the first reaction mixture is separated into top aqueous phase and bottom organic phase and the aqueous phase is then removed. The aqueous layer can be discharged from the top of the reactor. However, operating in this way can result in partial and possibly unsatisfactory removal of the aqueous phase, leaving some residual amounts of the aqueous phase in the reactor, and therefore it is generally preferred to discharge the entire content of the reactor, namely, both phases, from the bottom of the reactor and then perform the phase separation in a separate, suitable vessel, discarding the first aqueous phase and returning the first organic phase to a reaction vessel. The first organic phase which is collected and passed to the next stage is substantially free from residual aqueous phase, e.g., it is accompanied by not more than 15% (by weight), and preferably less than 5%, of the first aqueous phase. It is noted that the first aqueous phase which is removed contains an appreciable amount of sodium bromide, which may be recovered using conventional methods.

The first organic phase is then combined in a reactor with a second amount of aqueous alkali acrylate salt, to form a second reaction mixture. Preferably, the second amount of the sodium acrylate applied is sufficient to bring the reaction to completion, namely, it is from 10 to 30 molar % based on pentabromobenzyl bromide. The second reaction mixture is maintained under heating for a second period of time, designated herein $t_2$, which is generally not more than 90, e.g., between 60 and 80 minutes. The completion of the reaction can be confirmed by HPLC analysis, indicating that the remaining amount of PBBBr is preferably less than 0.5%, e.g., less than 0.2% (area).

Upon completing the reaction, water is added to the reaction vessel, and the second reaction mixture is allowed to separate into a second organic and a second aqueous phases.

The second organic phase is then recovered and the pentahalobenzyl acrylate product (e.g., pentabromobenzyl acrylate) is optionally isolated therefrom using conventional methods. For example, the second organic phase is washed with water (at 80° C.) and cooled to induce the crystallization of the product, which may then be separated from the slurry by filtration and drying. The washing is carried out with hot water, in a weight ratio of water to organic phase of ~1:5.

It is important to point out that mother liquor obtained from filtration of the product can be used in the process instead of fresh solvent.

The process set forth above for the preparation of PBBMA can be carried out either in a batch, semi-continuous or continuous mode of operation. For example, when the aqueous NaA reactant is added in two stages, then the reaction can be run employing two or more successively arranged reactors, divided between first and second reaction zones, with an intermediate phase separation step being carried out in a suitable settler located between the two reaction zones. The residence time expected in the overall reaction stage is about three hours. Thus, in the first reaction zone, ~85-90% NaA is introduced. The conversion, regarding NaA, will be complete within 1.5 hour, and two phases will be obtained. In the settler, the phases will be separated. The aqueous phase, which is mainly NaBr, will be the aqueous wastes or the stream from which NaBr can be separated. The organic phase will pass to the next (second) reaction zone. The remaining 10-15% NaA will be added continuously to the second reaction zone, and it is expected that the reaction will end within 1.5 h.

Thus, according to one embodiment of the invention, there is provided a process comprising continuously feeding into a first reaction zone a water immiscible organic solvent, pentahalobenzyl halide, a phase transfer catalyst and a first amount of an aqueous alkali acrylate salt, to form a first reaction mixture maintained under heating; continuously removing a reaction mass from said first reaction zone and separating said reaction mass into an organic and aqueous phases; continuously passing said organic phase to a second reaction zone into which a second amount of said aqueous alkali acrylate salt is being continuously supplied, and collecting a solution of the pentahalobenzyl acrylate product in said organic solvent and optionally isolating the pentahalobenzyl acrylate product in a solid form.

The continuous process is run through a set of successively arranged reactors, namely, a cascade of reactors, with a phase separator interposed between the reactors assigned to the first and second reaction zones. Thus, the first reaction zone is composed of a first group of reactor(s), e.g., two consecutively arranged continuously stirred reactors. Alternatively, the first reaction zone is provided by a tubular plug flow type reactor. The second reaction zone is provided in a similar manner. The reactors assigned to the first reaction zone are designated herein $R_{1i}$ (i=1, 2 . . . ) while the reactors belonging to the second reaction zone are designated $R_{2j}$ (j=1, 2 . . . ). Thus, the reactor in which all of the foregoing reactants and reagents are first brought into contact is $R_{11}$: the organic solvent (e.g., chlorobenzene or mother liquor), the pentahalobenzyl halide starting material (e.g., PBBBr), a solution of the phase transfer catalyst and the first portion of the aqueous sodium acrylate solution are concurrently fed into $R_{11}$, either by means of separate feed streams or various combinations. For example, a slurry of PBBBr in chlorobenzene, obtained by means of the radical bromination of pentabromotoluene in chlorobenzene, as described above, may be used as the combined feed of both chlorobenzene and PBBBr, usually together with some fresh amount of chlorobenzene. The feed rate of the materials is adjusted such that the residence time in each reactor is 45-55 min. The reaction mass flows from the $R_{11}$ reactor to the $R_{12}$ reactor, then it is discharged from the $R_{12}$ reactor and subjected to phase separation, following which the organic phase is passed to the $R_{21}$ reactor. Reactor residence time, as used herein, is the volume of the reactor contents divided by the flow rate at which the reaction mass is removed from the reactor. The volume of the organic phase is ~85% of the volume of the starting reaction mixture.

As may be appreciated in the light of the foregoing description, the total amount of aqueous sodium acrylate used in the process is divided between the first reaction zone and the second reaction zone. The amount of the aqueous sodium acrylate charged into the first reaction zone (i.e., $R_{11}$) is preferably from 80 to 90% of the total amount required for the complete reaction, and more preferably about 85-90% (e.g., 85-88%). The remaining 10-20% (more specifically 10-15%, e.g., 12-15%) of the NaA solution are continuously fed into the second reaction zone (the $R_{21}$ reactor).

The reactors $R_{1i}$ of the first reaction zone are held at a temperature in the range of 90° C. to 98° C. The reactors $R_{2i}$ of the second reaction zone are held at a temperature in the range of 90 to 98° C.

The pure monomer pentabromobenzyl acrylate prepared by means of the invention is collected in a solid form and can be polymerized to give the poly(pentabromobenzyl acrylate) flame retardant, using methods known in the art. For example, according to Example 1 of U.S. Pat. No. 4,128,709, the polymerization is accomplished in solution, using 2-methoxyethanol as a solvent. Poly (pentabromobenzyl acrylate) can also be produced by melt polymerization in an extruder, as described in U.S. Pat. No. 4,996,276. In U.S. Pat. No. 6,028,156, a polymerization in solution is described, using non-protic solvents such as methyl ethyl ketone or methyl isobutyl ketone.

It has now been found that the monomer pentabromobenzyl acrylate can undergo polymerization in solution using halogenated aromatic solvents such as chlorobenzene and 1,2-dichlorobenzene, to give poly(pentabromobenzyl acrylate). The solid monomer collected as set forth above is dissolved in fresh chlorobenzene, and polymerized according to the conditions described below. However, in a preferred embodiment of the invention, following the synthesis of the monomer in chlorobenzene, as outlined above, the second organic phase, consisting of the chlorobenzene solvent and the monomer pentabromobenzyl acrylate as a solute, is recovered and used (after having been washed with hot water), without isolating the monomer, in the polymerization reaction to give poly(pentabromobenzyl acrylate).

In general, the polymerization of PBBMA using halogenated aromatic solvents such as chlorobenzene is carried out with stirring and heating. The polymerization rate is faster in the presence of an initiator, namely, free radical initiator such as peroxide and azo compounds, e.g., dibenzoyl peroxide, dicumyl peroxide and 2,2-azodi-isobutyronitrile. The initiator loading is preferably between 0.5 and 3.0% w/w based on the monomer, preferably about 0.5 to 1.5%, e.g. 0.5-1.0%. However, it should be noted that the polymerization can take place at a reasonable rate even in the absence of any added initiator.

The concentration of the monomer in the chlorobenzene solvent is preferably from 40 to 65%, more preferably from 45 to 60%. The reaction vessel is heated, with the initiator (e.g., DPO or AIBN) being added either prior to the heating or when the temperature at the reaction vessel reaches about 50-60° C. The reaction typically starts at a temperature of about 85-90° C. The formation of the polymer is accompanied by a sharp rise of the temperature in the reaction mixture:

within a few minutes, the temperature of the reaction mixture may go up from about 90° to about 130° C. The greater the concentrations of the monomer and initiator are, the bigger is the change observed in the temperature of the reaction mixture. In order to obtain the polymer with the desired purity level (containing not more than about 1% w/w residual monomer), it is generally preferred to work with relatively high monomer concentration in the solvent (about 50-60% PBBMA solution) and initiator loading of not less than 0.5% w/w, e.g., 0.5-1.5% based on the monomer.

After stabilization of the temperature in the reactor, the heating continues further for 1-2 h at a temperature in the range from 110 to 130° C. in order to decompose the residual DBP initiator.

The polymer which is formed absorbs some of the solvent and constitutes a separate phase in the form of a viscous, honey-like material. During the cooling ($T_{reaction\ mixture} < 70°$ C.) it may change into a single lump even under strong stirring. Therefore, the isolation of the polymer product can be carried out by combining the hot reaction mixture with low alcohol under vigorous stirring when the reaction mixture is still sufficiently fluid, namely, when $T_{reaction\ mixture}$ is above 70° C. and before the solid polymer product forms a separate viscous phase. For example, the reaction mixture ($T_{reaction\ mixture} = 80°$) may be dropwise added to ethanol or isopropanol (at RT), under strong stirring. The slurry obtained is filtered, washed with a suitable alcohol and dried to obtain the polymer product.

Alternatively, the solid polymer product is isolated from the chlorobenzene solvent by evaporating the solvent. The product is then dried under vacuum at about 30 mmHg at 150-200° C. for a few hours.

The choice of solvent used in solution polymerization is significant. It has been found that the use of halogenated aromatic solvents in the solution polymerization of pentabromobenzyl acrylate offers several advantages. The polymerization reaction starts upon the decomposition of the initiator at about 80-90° and is associated with a strong heat release. The boiling point of the halogenated aromatic solvent is sufficiently high (about 135° C. and 180° C. in the case of chlorobenzene 1,2-dichlorobenzene, respectively) to allow the absorbance of the heat released by the polymerization reaction. Thus, halogenated aromatic solvents can act as a heat sink to prevent run-away reactions while significantly shortening the duration of the polymerization reaction, such that the reaction can rapidly reach completion within a workable temperature range (e.g., within less than 15 minutes at a temperature from 90° to 130° C.), while still running the process in a safe, controllable manner. The duration of the overall process, including the cooking time (namely, the heating stage which follows the polymerization reaction) is less than 180 minutes, and preferably less than 150 minutes, e.g., from 15 to 60 minutes. The experimental results reported below indicate that the solution polymerization of pentabromobenzyl acrylate in halogenated aromatic solvents such as chlorobenzene is significantly faster than corresponding polymerization reactions in other types of solvents. Furthermore, chlorobenzene can be easily removed from the finished polymer by evaporation to afford the product in an essentially pure form.

Accordingly, the invention also provides a solution polymerization process for preparing poly(pentabromobenzyl acrylate), comprising polymerizing the monomer pentabromobenzyl acrylate in halogenated aromatic solvent under heating, preferably in the presence of a free radical initiator. The polymerization can be carried out in a batch, semi-continuous or continuous mode of operation.

Poly (pentabromobenzyl acrylate) formed by means of solution polymerization of pentabromobenzyl acrylate in chlorobenzene has weight average molecular weight (Mw) in the range from 200,000 to 600,000 Da and number average molecular weight (Mn) in the range from 38,000 and 50,000, such that the polydispersity index, defined as the ratio Mw/Mn, is less than 15, preferably less than 13 and more preferably less than 10, e.g., from 5 to 10, based on high temperature gel permeation chromatography (in 1,2,4-trichlorobenzene at 120° C.) reported in detail below. The polydispersity index serves as an indication of the breadth of the molecular weight distribution of a polymer product. The thermal stability of the poly(pentabromobenzyl acrylate), as indicated by thermogravimetric analysis (TGA), which measures the weight of a sample as sample temperature is increased, is typically as follows:

TABLE 1

| temperature | T1 = 323 | T2 = 345 | T3 = 354 |
|---|---|---|---|
| % weight loss | 2.0 | 5.0 | 10.0 |

EXPERIMENTAL

HPLC analysis:
Pumping system: Agilent Technologies
Detector: 1200 series, $\lambda$=230 nm
Flow: 1.5 ml/min
Injection: 20 µl
Column: Kromasil, 5 u 100 A C18, 250×4.6 mm×5 µm
Solvents: Acetonitrile-85%
$H_2O$-15%
Retention times: PBBMA-9.2-9.4 min
PBBBr-12.4-12.7 min
5-BT-19.3-19.6 min High Temperature Gel Permeation Chromatography:
HT GPC instrument (Malvern Instruments Ltd.) was used to determine the molecular weight distributions of the polymer product. The instrument is equipped with refractive index (RI), viscometric (Visc), Low Angle Laser Scattering (LALLS) and Right Angle Laser Light Scattering (RALLS) detectors. Samples were dissolved in 1,2,4-trichlorobenzene (TCB) at 120° C. 5-7 mg/ml PBBPA solutions were prepared. 200 µL of the sample solution were injected into GPC columns. A series of three columns (2× Viscotek Mixed Bed LS+PLgel B mixed bed 10 µm) connected consecutively was used. TCB at 120° C. was used as the mobile phase with a flow rate of 0.8 ml/min. PolyCal PS-99K (Mw=98,851 Da; Mn=95,984 Da) standard was used for the calibration of the HT GPC. OmniSec software was used for the calculation of the Mn and Mw of the tested samples.

TGA Analysis:
The TGA analysis was performed by Hi-Res TGA 2950 Thermogravimetric Analyzer of TA Instruments using Pt crucible in N2 atmosphere with heating rate of 10 Grad/min in the range 35-700 grad C.

Example 1

Preparation of an Aqueous Solution of Sodium Acrylate, 37% w/w

Figure 1:
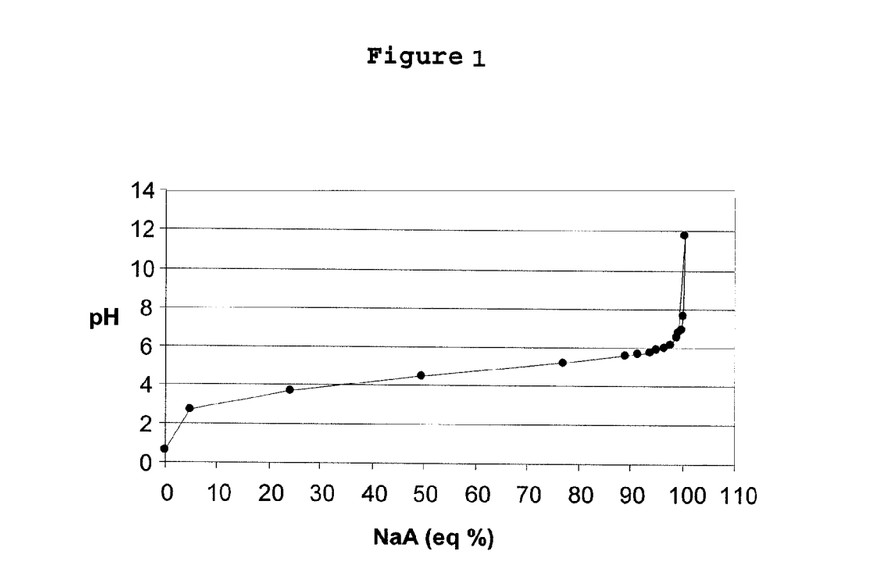
FIG. 1 shows a plot of the pH of the solution against the composition of the solution in accordance with Example 1.

In a stirred 1 L reactor with a cooling jacket ($T_j$=20° C.) was carried out a titration of acrylic acid (216 g, assay 98.7%, 2.961 mol) in water (284 g), with aqueous 47.8% sodium hydroxide (242 g, 2.892 mol) over 3 h. The reactor was equipped with a pH meter and changes during the titration were recorded. In FIG. 1, the pH of the solution is plotted against the composition of the solution. When the pH is about 6.2-6.3, a desired molar ratio between sodium acrylate and acrylic acid is obtained (97.5:2.5). This solution, which contains ~37% w/w dissolved material (sodium acrylate and acrylic acid), is stable at room temperature for several days.

Example 2

Preparation of an Aqueous Solution of Sodium Acrylate, 33% w/w

In a stirred 3 L reactor with a cooling jacket ($T_1$=20° C.) was carried out a titration of acrylic acid (730 g, assay 98.8%, 10.02 mol) in water (1260 g), with aqueous 48% sodium hydroxide (818 g, 9.82 mol) over 5 h. The reactor was equipped with a pH meter and changes during the titration were recorded. When the pH is about 6.3-6.4, a desired ratio between sodium acrylate and acrylic acid is obtained (98:2). This solution, which contains ~33% w/w dissolved material (sodium acrylate and acrylic acid), is stable at room temperature for several days.

Example 3

Preparation of pentabromobenzyl bromide

Into a one-liter jacketed reactor equipped with a mechanical stirrer (anchor type), condenser and thermocouple, were introduced chlorobenzene (390 g), water (390 g), 5-BT (390 g), dibenzoyl peroxide (6.4 g) and bromine (156 g) at room temperature and under stirring.

The mixture was then heated to 80° C. over 0.5 h and held at 80→90° C. for 2.5 h then at 90° C. for 3.5 h. The completion of the reaction was determined by GC analysis.

The reaction mixture was cooled to 52° C. and excess bromine was neutralized by the addition of aqueous 27% $NaHSO_3$ (60 g). The slurry obtained was cooled to 20° C. and the stirring stopped. The upper aqueous phase (522 g) was removed from the reactor from above, by suction with the aid of a peristaltic pump. To the mixture was added water (80 g) and an aqueous 10% solution of $Na_2CO_3$ (52 g), with stirring, at room temperature, to neutralize the acidity. The slurry was filtered on a Buchner and washed with CB (90 g) and water (120 g) at RT. The product was dried to constant weight in an evaporator at 90° C. and a vacuum of 15 mm Hg. Pure PBBBr (436 g) was obtained in a purity of 99.5%, by HPLC, area %. The yield of PBBBr was ~96%, based on 5-BT.

The filtrate and washings consisted of two phases. After phase separation, a heavy organic phase (404 g) and an aqueous phase (212 g) were obtained. Half the organic phase was retained for recycling to the reaction stage of the next run while the second half underwent fractional distillation to recover CB.

Example 4

Preparation of pentabromobenzyl acrylate by Means of a Batch Process

Into a 1 L jacketed reactor equipped with a mechanical stirrer (anchor type), a condenser and a thermocouple, were introduced chlorobenzene (425 g), aqueous 50% TBAB (9 g), PBBBr (425 g) and aqueous 35% NaA (180 g) at room temperature (20-25° C.) and with stirring. The reaction mixture was heated gradually to 95° C. over 1 h and held at a temperature of 94-95° C. for 1 h ($t_1$=60 min)

The reaction mixture was cooled to 85° C., removed from the reactor to a separating funnel and the phases were separated. The organic phase (849 g) was returned to the reactor, aqueous 35% NaA (36 g) was added, and the mixture was held at 94-95° C. for 75 min, with mechanical stirring ($t_2$=75 min)

The reaction was completed (PBBBr<0.1% by HPLC analysis) and the mixture was washed twice with water (2×190 g) at ~80° C. The organic solution (829 g, containing ~50% PBBMA) was cooled gradually to 5° C. to crystallize the PBBMA. The crystallization was carried out with seeding with pure PBBMA (~10 g) when the temperature in the reactor was ~40° C.

The slurry was filtered on a Buchner funnel. The product was dried to a constant weight in an evaporator at 50° C.→70° C.→90° C. gradually, and a vacuum of 30→15 mmHg Pure PBBMA (282 g) was obtained in a purity of 99.8% (by HPLC area %). The filtrate (520 g) contains ~25% dissolved material containing 99.2% PBBMA (based on HPLC area %).

~90% of the mother liquor was returned to the process in the next batch. The yield of the process was ~95%, based on PBBBr.

Example 5

Preparation of pentabromobenzyl acrylate by Means of a Batch Process

Into a 1 L jacketed reactor equipped with a mechanical stirrer (anchor type), a condenser and a thermocouple, were introduced chlorobenzene (425 g), aq. 50% TBAB (9 g), PBBBr (425 g) and aq. 35% NaA (180 g) at room temperature (20-25° C.) and with stirring. The reaction mixture was heated gradually to 95° C. over 1 h and held at a temperature of 94-95° C. for 1 h ($t_1$=60 min)

The reaction mixture was cooled to 80° C. and the aqueous phase (131 g) was removed from the top of the reactor by suction with the aid of a peristaltic pump. Aqueous 35% NaA (36 g) was added to the reactor and the mixture was held at 94-95° C. for 100 min ($t_2$=100 min), with mechanical stirring.

The work-up of the reaction mixture was carried out as for Example 4. The product and filtrate were obtained in similar yields and purities.

Example 6 (Comparative)

Preparation of pentabromobenzyl acrylate by Means of a Batch Process without Intermediate Phase Separation Into a 1 L jacketed reactor equipped with a mechanical stirrer (anchor type), a condenser and a thermocouple, were introduced chlorobenzene (425 g), aq. 50% TBAB (9 g), PBBBr (425 g) and aq. 35% NaA (216 g) at room temperature (20-25° C.) and with stirring. The reaction mixture was heated gradually to 95° C. over 1 h and held at a temperature of 94-95° C. for 4 h.

After completion of the reaction (PBBBr<0.5% by HPLC analysis) the mixture was washed three times with water (once with 110 g and twice with 190 g) at ~80° C., followed by phase separation. The organic solution (828 g, containing ~50% PBBMA) was cooled gradually to 5° C. to crystallize the PBBMA. The crystallization was carried out with seeding with pure PBBMA (~10 g) when the temperature in the reactor was ~40° C.

The slurry was filtered on a Buchner funnel. The product was dried to a constant weight in an evaporator at 50° C.→70° C.→90° C. gradually, and a vacuum of 30→15 mmHg Pure PBBMA (280 g) was obtained in a purity of 99.8% (by HPLC area %). The filtrate (523 g) contains ~25% dissolved material containing 99.2% PBBMA (based on HPLC area %).

Figure 2:
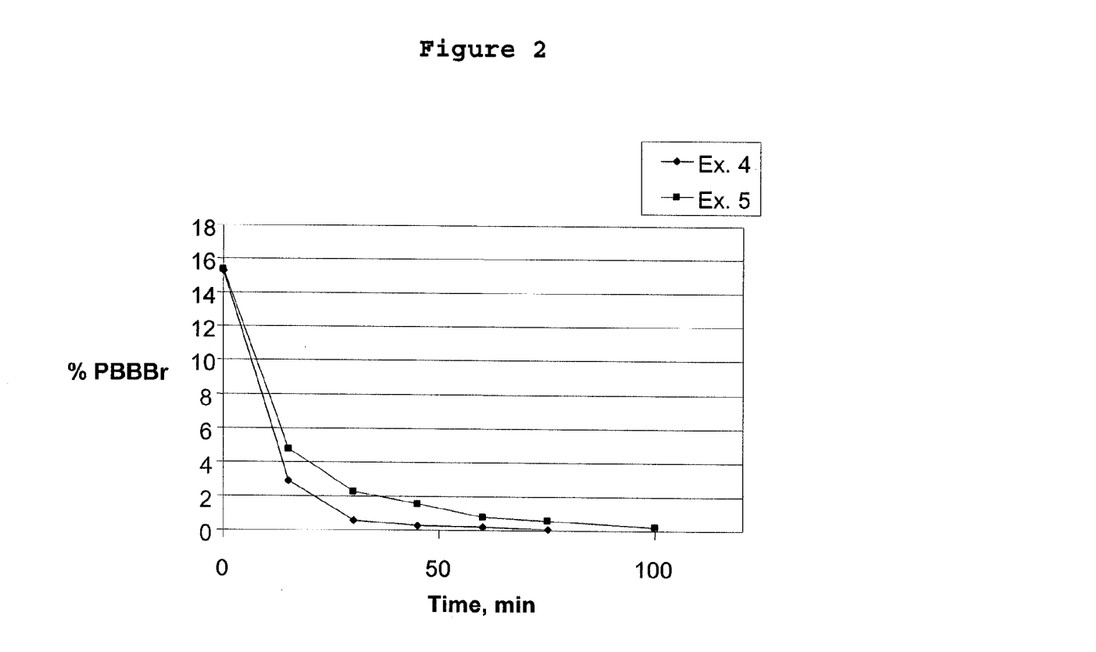
FIG. 2 shows results of the progress of the reactions after the step of phase separation, namely, during the second heating period (t2) in accordance with Examples 4 and 5.

The reaction mixtures according to Examples 4 and 5 were periodically sampled to determine their compositions at different times and the results of the progress of the reactions after the step of phase separation, namely, during the second heating period ($t_2$) are graphically presented in FIG. 2. Both reactions of Examples 4 and 5 lasted less than three hours and hence were significantly faster than the reaction of Example 6. If the gradual heating period at the beginning of the reactions, which was 60 minutes in all three cases, is not taken into account, then the total reaction time for Examples 4 and 5, which is given by $t_1+t_2$, was 60+60=120 minutes and 60+100=160 minutes, respectively, whereas the reaction according to Example 6 needed 240 minutes to reach completion (in case of Example 6, after 180 minutes, 0.8% PBBBr is present).

Although the progress of both reactions according to Examples 4 and 5 has been found to be satisfactory, FIG. 2 visibly reveals the superiority of the former over the latter. It is noted that after the first heating stage ($t_1$=60 minutes), both reactions achieved approximately the same level of PBBBr conversion (about 85%). However, the reaction of Example 4 was then "interrupted" to allow a quick and accurate phase separation, removal of the aqueous phase, return of the organic phase to the reaction vessel, following which the reaction was continued upon the addition of aqueous sodium acrylate and heating for a further duration of about $t_2$=60 minutes. The reaction was completed faster than in Example 5 ($t_2$=100 minutes), in which the phase separation was from the top of the reactor, which is less accurate.

Examples 7 and 8 (Both Comparative)

Investigating the Effect of the Presence of Sodium Bromide in the Aqueous Phase on the Progress of the Reaction Two comparative experiments on the preparation of PBBMA were carried out in a stirred 1 L reactor. The difference between the two experiments was that the second (Example 8) was carried out with the addition of NaBr from the start. The amount of NaBr added was about half the amount obtained at the end of a normal reaction.

Example 7

Into a 1 L jacketed reactor equipped with a mechanical stirrer (anchor type), a condenser and a thermocouple, were introduced mother liquor (520 g), chlorobenzene (40 g), aq. 50% TBAB (6.5 g), PBBBr (335 g) and aq. 37% NaA (159 g) at room temperature (20-25° C.) and with stirring. The reaction mixture was heated gradually to 95° C. over ~1 h and held at a temperature of 94-95° C. for 4 h.

After completion of the reaction (PBBBr<0.5% by HPLC analysis) the mixture was washed three times with water (once with 90 g and twice with 150 g) at ~80° C. The organic solution (872 g, containing ~50% PBBMA) was cooled gradually to 5° C. to crystallize the PBBMA. The crystallization was carried out with seeding with pure PBBMA (~10 g) when the temperature in the reactor was ~40° C.

The slurry was filtered on a Buchner funnel. The product was dried to a constant weight in an evaporator at 50° C.→70° C.→90° C. gradually, and a vacuum of 30→15 mmHg Pure PBBMA (302 g) was obtained in a purity of 99.8% (by HPLC area %). The filtrate (535 g) contains ~25% dissolved material containing ~95% PBBMA (based on HPLC area %).

Example 8

Into a 1 L jacketed reactor equipped with a mechanical stirrer (anchor type), a condenser and a thermocouple, were introduced mother liquor (520 g), chlorobenzene (40 g), aq. 50% TBAB (6.5 g), PBBBr (315 g) and aq. 37% NaA (159 g) and NaBr (30 g) at room temperature (20-25° C.) and with stirring. The reaction mixture was heated gradually to 95° C. over 1 h and held at a temperature of 94-95° C. for 5 h in order to complete the reaction (PBBBr<0.5% by HPLC analysis).

Figure 3:
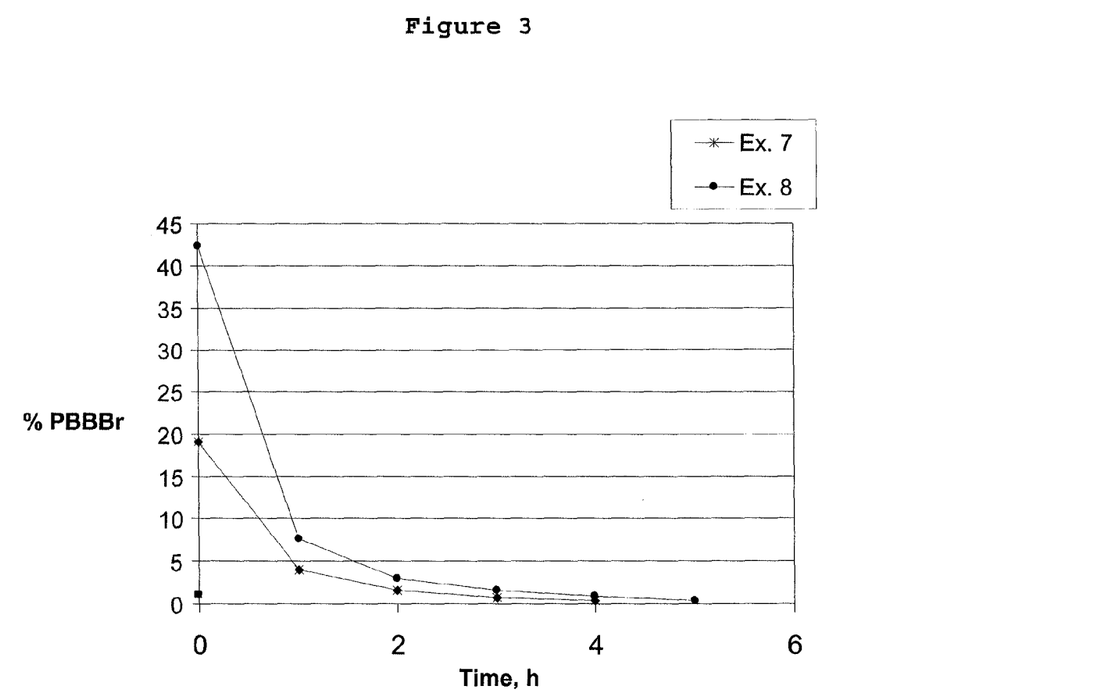
FIG. 3 shows the results of the progress of the reactions (t=0 corresponds to the end of the gradual heating stage, following which the reaction was kept at temperature of 94-95° C. for several hours) in accordance with Examples 7 and 8.

The reaction mixtures according to Examples 7 and 8 were periodically sampled to determine their compositions at different times and the results of the progress of the reactions are presented in FIG. 3 (t=0 corresponds to the end of the gradual heating stage, following which the reaction was kept at temperature of 94-95° C. for several hours).

Upon comparing the results which are graphically presented in FIG. 3, it can be clearly seen that the disappearance of the PBBBr in Example 7 is faster than in Example 8, demonstrating that there is an inverse correlation between the amount of sodium bromide present in the aqueous phase and the rate of the reaction.

Example 9

Preparation of Pentabromobenzyl Acrylate Solution by Means of a Continuous Process The experimental set-up used for the continuous process for the preparation of PBBMA consists of the following:
two stirred reactors heated to 94-98° C. with a working volume of 250 ml each, connected via the side exit;
continuous, heated phase separator;
two stirred reactors heated to 94-98° C. with a working volume of 220 ml each;
collection flasks at the end of the system.

In general, the continuous mode of operation consists of feeding into the first reactor chlorobenzene, PBBBr, aqueous 50% TBAB solution, and the first portion of the aqueous 35% NaA solution. The feed rate of the materials is such that the residence time in each reactor is 0.8-0.9 h. After the first two reactors is a phase separator from which the organic phase passes into the third reactor into which is also fed the second part of the aqueous NaA. After the fourth reactor, the PBBMA solution in chlorobenzene is collected, washed with hot water and analysed.

The following experiment was carried out according to the general procedure outlined above. Into the first reactor, which was heated to 94-98° C., were introduced the following materials at rates of:
Chlorobenzene 163 g/h
PBBBr 163 g/h
aq. 35% NaA 67 g/h
aq. 50% TBAB 4 g/h After phase separation, the hot organic phase was transferred to the third reactor at a rate of ~330 g/h, where the second part of the aqueous 35% NaA was added at a rate of 12 g/h.

After 16 h (net) working time (controlled by HPLC analysis) the collected solution was washed with hot water (1100 g). An organic solution was obtained (4982 g) containing ~2441 g crude PBBMA. The content of PBBBr in the product was less than 0.2% (by HPLC, area %).

Example 10 (Comparative)

Preparation of Pentabromobenzyl Acrylate Solution by Means of a Continuous Process without Phase Separation The experimental set-up used for the continuous process for the preparation of PBBMA, without phase separation, consists of the following:

Four stirred reactors heated to 94-98° C. with a working volume of 250 ml each, connected via the side exit;

collection flasks at the end of the system.

In general, the continuous mode of operation consists of feeding into the first reactor chlorobenzene, PBBBr, aqueous 50% TBAB solution, and the aqueous 35% NaA solution. The feed rate of the materials is such that the residence time in each reactor is ~0.9 h. After the fourth reactor, the PBBMA solution in chlorobenzene is collected, washed with hot water and analysed.

The following experiment was carried out according to the general procedure outlined above. Into the first reactor, which was heated to 94-98° C., were introduced the following materials at rates of:

Chlorobenzene 163 g/h
PBBBr 163 g/h
aq. 35% NaA 70 g/h
aq. 50% TBAB 4 g/h

After 16 h (net) working time (controlled by HPLC analysis) the collected solution was washed with hot water (2×1000 g). An organic solution was obtained (4970 g) containing ~2435 g PBBMA. The content of PBBBr in the product was ~1.3% (by HPLC, area %).

Examples 11-23

Polymerization of Pentabromobenzyl Acrylate in Chlorobenzene to Give Poly(Pentabromobenzyl Acrylate)

A number of experiments were carried out on the polymerization of pure PBBMA, using chlorobenzene as solvent. Some of the experiments were carried out in the presence of DBP catalyst, and some without catalyst. In general, the polymerization reaction takes place at $T_R \geq 90°$ C. ($T_R$ indicates the temperature in the reactor at which polymerization starts) within a few minutes and the temperature in the reactor goes up suddenly. After stabilization of the temperature in the reactor, the cooking continues further for 1-2 h in order to decompose the residual DBP initiator.

Isolation of the product was carried out by adding the reaction mixture (at temperature of about 80° C.) dropwise to an alcohol (ethanol, 2-propanol or 1-propanol at RT), under strong stirring. The slurry obtained was filtered, washed with alcohol and dried to constant weight. The reaction conditions and results of the concentrations of residual monomer (RM) in the product are presented in Table 2.

TABLE 2

| Example | CB g | PBBMA g | DBP g | $T_R$ °C. | $T_{RM}$ °C. | $t_{pol}$ min | $t_{total}$ h | RM % |
|---|---|---|---|---|---|---|---|---|
| 11 | 100 | 56 | 0.3 | 85-90 | 95 | ~10 | 2.5 | 1.7 |
| 12 | 100 | 56 | 0.6 | 95-100 | 114 | ~10 | 2.0 | 1.1 |
| 13 | 100 | 56 | — | 132-134 | — | — | 4.0 | 4.8 |
| 14 | 100 | 56 | — | 132-135 | — | — | 8.0 | 2.0 |
| 15 | 80 | 100 | — | 135-138 | — | — | 3.0 | 4.9 |
| 16 | 80 | 100 | 0.5 | 90-100 | 125 | ~6 | 2.0 | 1.0 |
| 17 | 80 | 100 | 0.2 | 90-100 | 114 | ~6 | 3.0 | 2.7 |

$T_R$—Temperature in reactor at which polymerization starts
$T_{RM}$—Maximum temperature in the reactor during the polymerization reaction
$t_{pol}$—Polymerization time: heating and returning to s.p. temperature
$t_{total}$—Time of overall process, including cooking
RM—Residual monomer in the PBBPA product after isolation From the results reported in Table 2 it can be seen that the polymerization of pure PBBMA in CB takes place even without catalyst.

The polymerization reaction according to the procedure outlined above was repeated, varying the concentration of the monomer and the catalyst loading. Instead of fresh chlorobenzene, a solution of PBBMAr in chlorobenzene, obtained following the synthesis of the monomer, was employed directly in the polymerization reaction. The course of the polymerization was the same in all the experiments: heating of the reaction mixture to 90° C., a sudden rise in the temperature of the reaction mixture over 2-3 mins, then cooking at 110° C. for 1 h. At the end of the process the solvent was evaporated (at a vacuum of 30→10 mm Hg and 95° C.) and the product was checked by HPLC to determine the RM. The results are presented in Table 3.

TABLE 3

| Solution of PBBMA | | PBBMA | DBP | $T_R$* | PBBPA | RM |
|---|---|---|---|---|---|---|
| g | % | g | mg | °C. | g | % |
| 18 | 195 | 35 | 68.3 | 340 | 90 –> 98 | 68.6 | 3.3 |
| 19 | 203 | 35 | 71.1 | 711 | 90 –> 104 | 72.0 | 3.3 |
| 20 | 156 | 47 | 73.3 | 370 | 90 –> 115 | 73.2 | 2.6 |
| 21 | 146 | 47 | 68.6 | 690 | 90 –> 118 | 70.0 | 2.1 |
| 22 | 134 | 61 | 81.7 | 410 | 90 –> 126 | 81.9 | 1.2 |
| 23 | 134 | 61 | 81.7 | 800 | 90 –> 128 | 82.3 | 0.9 |

DBP—Dibenzoyl peroxide (75%)
*$T_R$—Change in temperature in the reactor during the polymerization over 2-3 min The starting concentration of the DBP and PBBMA in CB has an affect on the RM content in the product. In order to obtain PBBPA containing ~1% w/w RM, the polymerization is preferably carried out on ~60% PBBMA solution and the recommended concentration of DBP is 0.5-1%, based on PBBMA.

Examples 24-30

Polymerization of Pentabromobenzyl Acrylate in Chlorobenzene to Give Poly(Pentabromobenzyl Acrylate)

The next set of examples illustrates the solution polymerization of PBBMA using chlorobenzene as the solvent, in the presence of dibenzoyl peroxide (DBP) and 2,2-azodi(isobutyronitrile) (AIBN) as the initiator, with mechanical stirring and heating to 80-90° C. The concentration of the monomer in chlorobenzene was 60% w/v and the quantity of the initiators AIBN and DBP (containing ~25% water) was ~1% w/w to PBBMA.

The reaction takes place within a few minutes in the presence of DBP and AIBN, and the temperature in the flask goes up suddenly. The cooking is allowed to continue for a further time (15 min or 60 min) The polymer which was formed absorbed the solvent and was in the form of a viscous, honey-like material. During the cooling ($T_R$<70° C.), it changed to a single lump, even under strong stirring. Samples were dried and analyzed for residual monomer (RM), Mw and Mn. The results are summarized in Table 4.

TABLE 4

| Example | Initiator | $T_R$* ° C. | Time (min) | RM % | Mw KDa | Mn KDa | PD |
|---|---|---|---|---|---|---|---|
| 24 | DBP | 90 –> 116 | 15 | 1.6 | 232 | 43 | 5.4 |
| 25 | DBP | 92 –> 117 | 60 | 1.3 | 381 | 50 | 7.6 |
| 26 | DBP | 100 –> 128 | 60 | 1.0 | 310 | 48 | 6.5 |
| 28 | AIBN | 80 –> 104 | 15 | 0.9 | 555 | 45 | 12.3 |
| 29 | AIBN | 82 –> 113 | 60 | 1.3 | 513 | 38 | 13.5 |
| 30 | AIBN | 82 –> 124 | 60 | 1.2 | 554 | 50 | 11.1 |

*$T_R$—Change in temperature in the reactor during the polymerization over 2-3 min For the purpose of comparison, the conditions of solution polymerization reactions of the monomer pentabromobenzyl acrylate reported in U.S. Pat. No. 4,128,709 and U.S. Pat. No. 6,028,156 are set out in Table 5 below (the solvent used, the amount of initiator present in the solution, the temperature and duration of the polymerization reaction):

TABLE 5

| Example | solvent | Temperature ° C. | Initiator % w/w* | Time hours |
|---|---|---|---|---|
| U.S. Pat. No. 4,128,709 Example 1 | Methyl glycol | 80-120 | ~3% | ~10 |
| U.S. Pat. No. 4,128,709 Example 2 | Methyl glycol | 120 | ~2% | 15 |
| U.S. Pat. No. 6,028,156 Example 2 | Methyl ethyl ketone | 75 | 2 | 6 |
| U.S. Pat. No. 6,028,156 Example 3 | Methyl isobutyl ketone | 110 | 2 | 6 |
| U.S. Pat. No. 6,028,156 Example 4 | Methyl ethyl ketone | Reflux (~80° C.) | 0.3 | 3 |
| U.S. Pat. No. 6,028,156 Example 6 | Cyclohexane | 81 | 2 | 7 |
| U.S. Pat. No. 6,028,156 Example 7 | Diethylene glycol-dimethyl ether | 80 | 2 | 7 |
| U.S. Pat. No. 6,028,156 Example 8 | ethylene glycol-dimethyl ether | 70 | 2 | 8 |
| U.S. Pat. No. 6,028,156 Example 9 | p-dioxane | 70 | 2 | 8 |

*w/w relative to the monomer

The invention claimed is:

1. Poly (pentabromobenzyl acrylate) having a weight average molecular weight (Mw) in the range from 200,000 to 600,000 and a polydispersity index less than 15 based on high temperature gel permeation chromatography.

2. Poly (pentabromobenzyl acrylate) according to claim 1, wherein the polydispersity index is less than 10.

3. Poly (pentabromobenzyl acrylate) according to claim 1, wherein the polydispersity index is from 5 to 10.

* * * * *